(12) United States Patent
Petrich et al.

(10) Patent No.: US 6,362,890 B1
(45) Date of Patent: Mar. 26, 2002

(54) METHOD AND DEVICE FOR CHECKING THE LIQUID TAKE UP OF A TEST LAYER OF AN ANALYSIS ELEMENT

(75) Inventors: Wolfgang Petrich, Bad Schoenborn; Uwe Ruppender, Mannheim; Dirk Voelkel, Heidelberg, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/591,269

(22) Filed: Jun. 9, 2000

(30) Foreign Application Priority Data

Jun. 14, 1999 (DE) .......................................... 199 26 931

(51) Int. Cl.$^7$ .............................................. G01N 21/00
(52) U.S. Cl. ...................................... 356/432; 356/436
(58) Field of Search ................................ 356/432, 435, 356/436, 440, 426, 427, 244, 246, 39, 40; 250/573, 576; 422/68.1, 73; 436/172, 169, 805

(56) References Cited

U.S. PATENT DOCUMENTS

| | | | | |
|---|---|---|---|---|
| 3,907,503 A | * | 9/1975 | Betts et al. ................ 23/253 R |
| 4,810,658 A | * | 3/1989 | Shanks et al. ............... 436/172 |
| 4,985,205 A | | 1/1991 | Fritsche et al. ............... 422/56 |
| 5,096,836 A | | 3/1992 | Macho et al. ............... 436/169 |
| 5,114,350 A | | 5/1992 | Hewett ........................ 435/288 |
| 5,169,787 A | | 12/1992 | Knappe et al. ............. 436/169 |
| 5,221,958 A | | 6/1993 | Bohnenkamp ............... 356/318 |
| 5,424,035 A | | 6/1995 | Hones et al. .................. 422/55 |
| 5,463,467 A | | 10/1995 | Baumann et al. ........... 356/446 |
| 5,536,470 A | | 7/1996 | Frey et al. ..................... 422/56 |
| 5,563,042 A | | 10/1996 | Phillips et al. ................ 435/14 |
| 5,616,922 A | | 4/1997 | Reffner et al. ......... 250/339.12 |
| 6,071,251 A | * | 6/2000 | Cunningham et al. ...... 600/584 |
| 6,084,660 A | * | 7/2000 | Shartle ........................ 356/39 |

FOREIGN PATENT DOCUMENTS

| | | | | |
|---|---|---|---|---|
| DE | 42 27 665 A1 | 2/1994 | .......... G01N/33/52 |
| DE | 43 05 058 A1 | 8/1994 | .......... G01N/33/48 |
| DE | 4407749 | 9/1994 | |
| DE | 196 28 562 A1 | 1/1998 | .......... G01N/35/02 |
| EP | 0 087 466 B1 | 1/1988 | .......... G01N/35/02 |
| EP | 0 473 241 A2 | 3/1992 | .......... G01N/33/52 |

\* cited by examiner

*Primary Examiner*—Frank G. Font
*Assistant Examiner*—Michael P. Stafira

(57) ABSTRACT

Method and device for checking the liquid take up of a test layer of an analysis element. The test layer is absorbent and takes up a liquid when an analysis is carried out. The test layer is illuminated with primary light to generate a light signal characteristic of the liquid take up. Secondary light emerging here from the analysis element is detected. The test layer is in contact with an optically transparent foil segment. Reliably checking liquid take up is achieved by detecting secondary light emerging from the circumferential surface of the foil.

32 Claims, 3 Drawing Sheets

METHOD AND DEVICE FOR CHECKING THE LIQUID TAKE UP OF A TEST LAYER OF AN ANALYSIS ELEMENT

FIELD OF THE INVENTION

The present invention is concerned with a method to check the liquid take up of a test layer of an analysis element, as well as a corresponding analytical system comprising analysis elements and an evaluation instrument designed to evaluate them.

BACKGROUND AND SUMMARY OF THE INVENTION

So-called carrier-bound tests are used on a large scale to analyze the components in a liquid sample qualitatively and quantitatively, particularly in body fluids of humans or animals. In such tests analysis elements are used where reagents are embedded into one or more test layers. An analysis element is brought into contact with the sample to carry out a reaction. The reaction of the sample and reagent results in a change in the analysis element that is characteristic for the analysis and can be evaluated visually or with the aid of an evaluation instrument (usually by reflection photometry).

The evaluation instrument is generally suitable for evaluating a special type of analysis element from a particular manufacturer. Thus, the analysis elements and the evaluation instrument form mutually matched components and are together usually designated as an analytical system.

Numerous different analysis element types are known which vary with respect to the measuring principle (e.g. optical or electro-chemical) and reagents used as well as other design features, in particular the arrangement and fixation of the test layers. Strip-shaped analysis elements (test strips) are particularly common, which comprise a lengthy plastic strip ("base strip") and at least one test layer affixed to it. Another common analysis element type uses a plastic frame similar to a photographic slide, framing at least one test layer.

Test layers comprise an absorbent material, such as paper or porous plastic. When brought into contact with the liquid sample to carry out an analysis, they absorb liquid. For correct analysis, it is important that the liquid is taken up regularly and completely. In each test the same quantity of liquid corresponding to the absorbency of the test layer is to be taken up and evenly distributed on the test layer.

Visually checking liquid take up by the user is not very reliable. This is particularly true in the case of analysis elements for checking the blood-sugar level used by diabetics, whose sight is frequently impaired by their illness. This is why numerous proposals have already been made to check the liquid taken up by test layers with technical equipment using a measuring method carried out by the evaluation instrument.

For example, in EP-0087466, an analytical system is described in which the quantity of the sample taken up by the test layer is estimated, based on the optical absorption of water in the infrared range. To generate a light signal characteristic of the liquid take up, the test layer is illuminated with primary light (infrared light with a wavelength of some 2 $\mu$m), and the secondary light diffusely reflected from the test layer is detected using a light receiver. The intensity of the reflected light is determined when the analysis element is dry as well as after it was contacted with the sample. To obtain information about the quantity of liquid taken up in the test layer, the difference between the two light signals is compared with a reference signal.

Further known methods using an evaluation instrument to check that test layers completely absorb the liquid are described in EP 0473241 A2, U.S. Pat. No. 5,114,350 and DE 19628562 A1. A common feature of these known methods is that the test layer's surface is illuminated with primary light, and that the intensity of the light diffusely reflected by the test layer is observed by means of a detector directed onto the test layer's surface while the liquid is being taken up in the layer. The liquid penetrating the test layer causes a reduction of the diffusely reflected intensity. The point in time and degree of change in intensity of the diffusely reflected light is used to obtain information about the point in time and completeness of the liquid taken up in the test layer.

This known measuring principle, however, has considerable disadvantages. In particular, the magnitude of the signal change with liquid take up is very much dependent on the optical absorption of the liquid at the measuring wavelength of the primary light. This is why in the spectral area of visible light an easily measurable, strong signal change only occurs with strongly colored liquids, such as whole blood. If, on the other hand, the liquid taken up into the test layer is only very slightly colored in the visible spectrum (as, for example, with serum or urine), the signal change is very small, and the checking of liquid take up therefore unreliable. It is in particular sensitive to disturbances, such as slight alterations in the position of the test layer caused by unintentional touching of the analysis element in the evaluation instrument.

On this basis, the invention addresses the problem of providing a method and a device for checking the liquid take up of a test layer with improved reliability.

This problem is solved by a method in accordance with claim 1 and an analytical system in accordance with claim 5. Preferred designs are the subject matter of the subclaims.

Numerous different types of analysis elements are known for which the invention can be advantageously used.

In a common type of analysis elements a plurality of test layers are arranged over one another in such a way that their main surfaces are in contact with each other, allowing an exchange of liquid therethrough. The test layers stacked over one another are together designated as the "test field". The sample liquid is usually applied onto the topmost layer of the test field and gradually penetrates the test layers underneath until finally the lowest layer takes up the liquid. Due to the fact that the liquid is basically distributed perpendicular to the test layers' main surface direction with such analysis elements, they are designated as "analysis elements with perpendicular liquid transport".

In "analysis elements with longitudinal liquid transport", several test layers are arranged—usually on a base strip— directly next to one another, whereby they are held together in contact on the edge, enabling liquid to pass over from test layer to test layer parallel to their main surface direction.

Finally, combinations of these two principles are known, as, for example, described in U.S. Pat. No. 5,096,836.

As a rule, checking liquid take up refers to the last test layer in the path of liquid flow of the analysis element. In principle, however, the invention is suitable for checking the liquid take up of any absorbent test layer of an analysis element, insofar that this test layer is in direct contact with an optically transparent foil segment. Here, the term "absorbent" is generally to be understood as a designation for any form of liquid take up and not only includes absorbency by porous materials caused by capillary effect, but also liquid take up based on a swelling process.

In the design of analysis elements optically transparent plastic foils are mainly used as test layer carriers, where the test layer is permanently fixed to a foil segment. In particular, the foil segment forming a test layer carrier may be directly coated with the test layer. This is customary for test layers which do not have self-supporting properties.

An example of this type of test layers are so-called test films, i.e. test layers manufactured by coating a substrate with a thin film of a film-forming material. In particular, test films capable of swelling on the basis of gelatine as well as non-swelling porous test films on the basis of a dispersion film former are known. The film-forming mass used to form such a film generally comprises, apart from reagents, solid components, such as pigments and diatomaceous earth that provide the desired opacity and absorbency. The invention is in particular suitable for test layers comprising a dispersion film former and a pigment. Such test layers are described, for example, in U.S. Pat. No. 5,169,787 and 5,536,470.

The transparent foils used in analysis elements (particularly as test layer carrier foil) have a very small thickness of usually less than 0.2 mm. The surface area of the circumferential surface (i.e. of the surface generated by cutting the foil and running vertical to the foil's main surface direction on its circumference) is accordingly very small. With a square foil segment with 6 mm edge length, for example, the circumferential surface comprises four sections that each have an area of only 1.2 mm$^2$, compared to which the main surfaces (topside and underside) each have a surface area of 36 mm$^2$. Consequently the exit cross-section for light from the circumferential surface is very small, but it has been determined within the scope of the invention that the intensity of light emerging from the circumferential surface is high enough to be measured without difficulty.

A particular advantage is that the percentage change in the intensity of light coming from the circumferential surface during liquid take up is considerably higher than the intensity change of the diffusely reflected light detected in the known methods of checking liquid take up. This is in particular true even in cases, in which the liquid taken up by the test layer has a weak color. A relatively strong signal change is observed even when the test layer takes up distilled water. Therefore the method according to the invention achieves with simple means an increased reliability for checking liquid take up. The method is very robust against disturbances, such as changes in primary light or in the position of the analysis element in the evaluation instrument caused by involuntary contact.

The method according to the invention selectively detects the moistening of the limiting layer between the test layer and the foil segment. Complete liquid take up is therefore more reliably detected than with the known methods, in which the measuring signal refers to the average value of the test layer volume.

BRIEF DESCRIPTION OF THE DRAWINGS

The invention is described in greater detail below with embodiments schematically presented in the figures wherein.

DETAILED DESCRIPTION OF THE DRAWINGS

Figure 1:
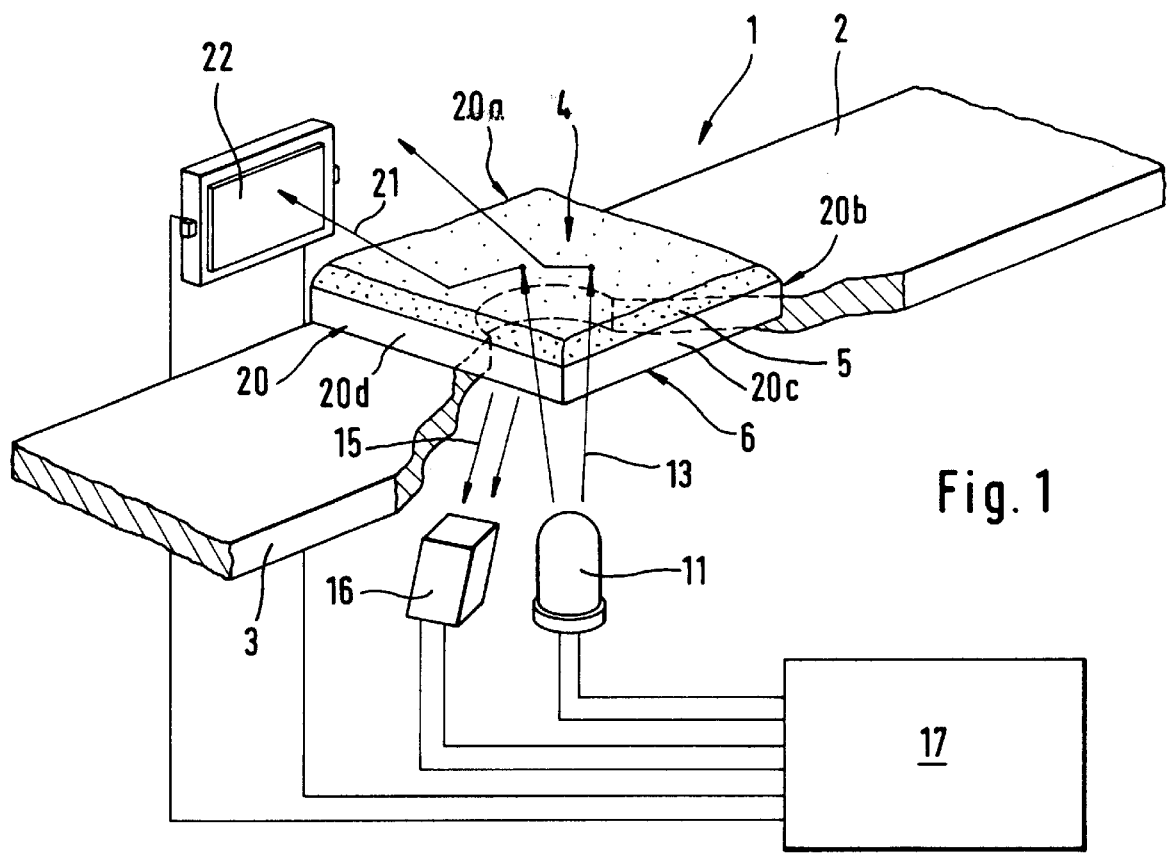
FIG. 1 shows a perspective principal presentation of those elements of an analytical system, which are important for the invention.
Figure 2:
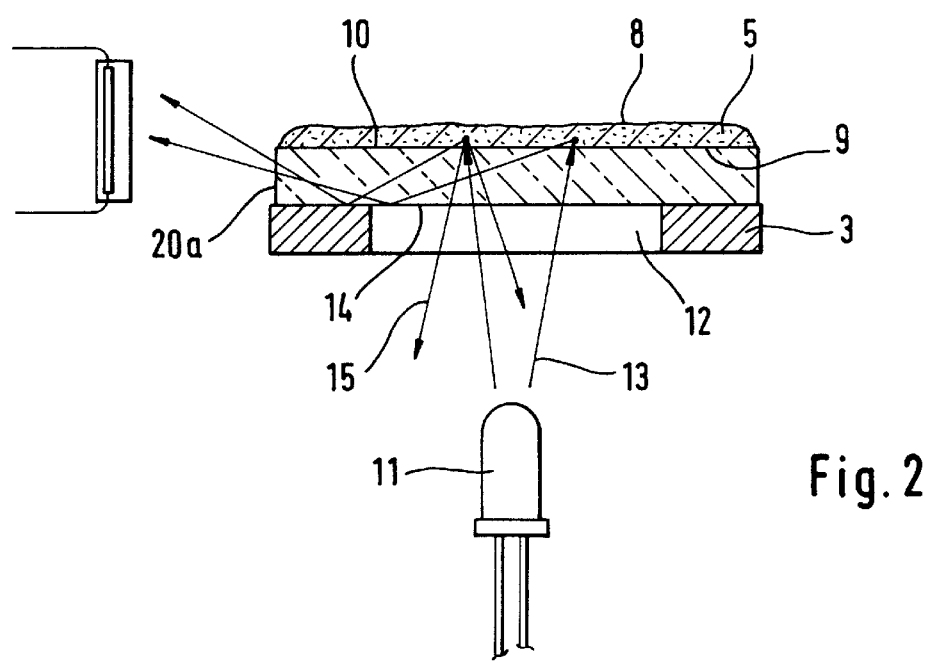
FIG. 2 shows a side view, partly in section, corresponding to FIG. 1.

The analysis element 1 shown in FIGS. 1 and 2 is formed as a test strip 2. It comprises a base strip 3 manufactured from rigid plastic and a test field 4 affixed on it. In the case shown, the test field 4 only has one test layer 5 firmly connected with a foil segment 6.

A drop of the sample liquid is placed on the topside 8 of the test layer 5 to carry out an analysis. The liquid dissolves the reagents contained in the test layer 5 and penetrates until it comes on the underside 9 of the test layer 5 into contact with the topside 10 of the foil segment 6.

The reaction of the analyte contained in the sample results in an optically measurable change, in particular a change in color, of the test layer 5. For measuring this change, the evaluation instrument has a light source 11, for example an LED, whose primary light 13 is directed through a hole 12 provided underneath the test field 4 of the base strip 3 onto the underside 14 of the foil segment 6. The secondary light diffusely reflected by the test layer 5 through the foil segment 6 (symbolized here by the arrow 15) is converted by a light receiver 16 into measurement signals. These signals are further processed by an evaluation electronics 17 into information about the presence or concentration of the analyte in the sample.

In so far the analytical system shown and the measuring method are conventional. Checking of the light source 11 and evaluation of the measurement are performed in known manner with the help of the evaluation electronics 17 usually working with a microprocessor.

To detect the light coming from the circumferential surface 20 of the foil segment 6 (symbolized in the figures by the arrows 21), a light receiver 22 is provided which is also connected to the evaluation electronics 17. To differentiate it from the measuring receiver 16, it is subsequently designated as checking receiver 22. The designation "transversal signal" is subsequently used for its light signal, while the signal of the measuring receiver 16 is designated as a "remission signal".

The checking receiver 22 must be designed and arranged in such a way that it selectively detects secondary light emerging from the circumferential surface 20. One example of how this can be simply achieved is shown in FIG. 3.

Figure 3:
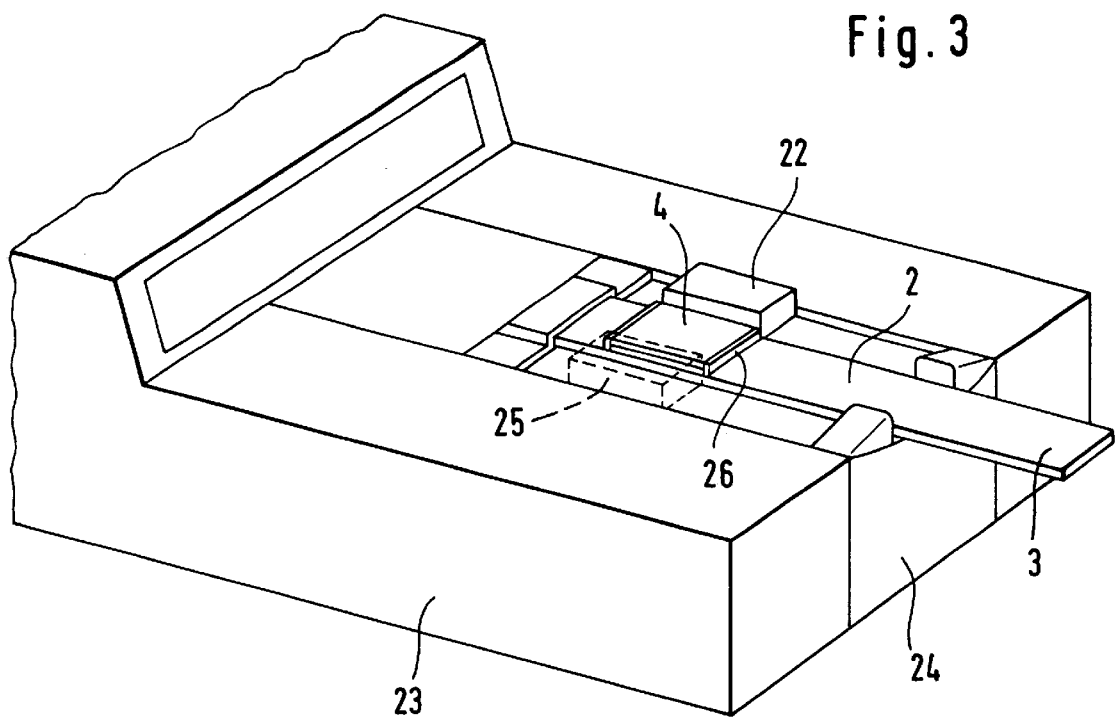
FIG. 3 shows a perspective presentation of a part of the evaluation instrument, having a holder in which an analysis element is fixed in a measuring position.

The evaluation instrument 23 shown in FIG. 3 has a test strip holder 24 to hold the test strip 2 in a defined measuring position. A suitable test strip holder is described, for example, in U.S. Pat. No. 5,424,035. The checking receiver 22 is positioned in such a way that its light-sensitive area is closely adjacent to the circumferential surface 20. Additional means may be provided to minimize disturbances from other light sources, in particular from diffuse primary light or from ambient light. This can be, as known, screens, light block-off walls or a cover sealing the analysis element holder 24 so that no light may enter. Moreover, it can be expedient to use frequency-modulated primary light and a detection method selective for the modulation frequency.

Due to the fact that the test field shown in the figures—as generally usual—is rectangular in shape, the circumferential surface 20 comprises four sectional areas 20a to 20d each running between the corners of the rectangle. To generate as great a transversal signal as possible, it may be advantageous to record the light emerging from the circumferential surface 20 in all directions, using a plurality of checking receivers, which are each positioned in such a way that they detect secondary light coming from any one of the sectional areas 20a to 20c on the circumferential surface 20. A second checking receiver 25 is shown in FIG. 2 as a dotted line, designed analogous to the checking receiver 22 and positioned on the opposite side of the test field 4, so that light emerging from the two lateral sectional areas 20a and 20c of the circumferential surface 20 of the foil segment 6 can be detected. With the type of test strip shown, the two remaining (front and back) sectional areas of the circumferential surface are not accessible, because they are sealed by a melt adhesive strip 26, serving to attach the test field 4 on the base strip 3.

To increase the intensity of light emerging from the sectional area 20a of the circumferential surface 20, it may be advantageous to provide at least one of the other sectional areas 20b to 20d of the circumferential surface 20 with a specular reflecting layer, so that the specular reflected light emerges from the circumferential surface 20 in the direction of the checking receiver 22.

The following experimental results were obtained with the arrangement shown in FIG. 3 with only one checking receiver 22. They show that very good results can be achieved even if the secondary light emerging from only one of the four sectional areas 20a to 20d of the circumferential surface 20 is used to check the liquid take up.

Figure 4:
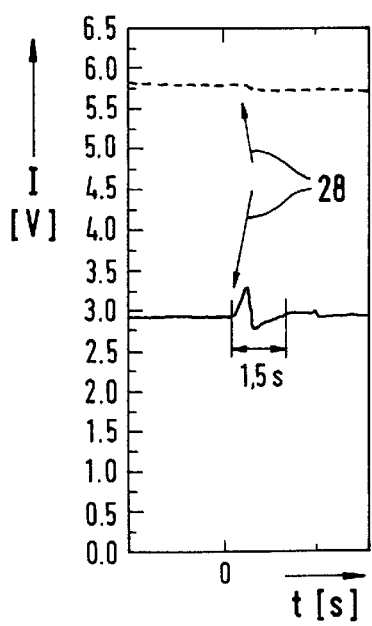
FIG. 4 shows measuring curves during checking of the liquid take up of an analysis element with blood as the sample liquid.

FIG. 4 shows the course of the light signal during the liquid take up into the test layer 5. The intensity I (voltage of the amplified signal in volts) is shown as a function of time t (measured in seconds). The top dotted line shows the remission signal, i.e. the intensity detected by the measuring receiver 16 of the diffusely reflected secondary light. The full bottom line shows the transversal signal, i.e. the intensity of the secondary light coming from the circumferential surface 20 detected by the checking receiver 22. These two light signals were amplified with identical amplifiers. The arrows 28 indicate the point in time, when the surface of the test layer 5 was contacted by the liquid sample.

The intensity of the remission signal is twice as high as that of the transversal signal. For measuring precision, it is, however, considerably more important that the relative signal change of the transversal signal is substantially greater than that of the remission signal. The remission signal drops so slightly (by some 1.3% on an average over five series of measurements) at the point in time when the liquid is taken up that it can be reliably evaluated only with great difficulty. In contrast, the transversal signal rises considerably more (by some 5% on an average over five measurements) while the liquid is being taken up into the test layer. This increase can be evaluated relatively easily and reliably. It can be particularly useful to differentiate the time dependence of the light signal with a differentiator contained in the evaluation electronics 17, thereby to detect the signal change with high reliability. It may also be advantageous to set the transversal signal received by the checking receiver 22 in relation to the remission signal of the measuring receiver 16 and to base further evaluation for checking liquid take up on the quotient or the difference of the two signals.

According to the inventors' present knowledge, the effect on which the invention is based is probably to be attributed to the fact that the conditions for coupling the light out of the foil segment are changed by the moistening of the test layer 5 and therefore the topside 10 of the foil segment 6 facing the test layer 5 is moistened. Some of the primary light 13 penetrating the foil segment (dependent on the angle of incidence) is totally reflected at the boundaries of the foil segment 6. Therefore the foil segment acts to a certain degree as a light conductor. The totally reflected light emerges from the circumferential surface 20 and can be detected as described.

Figure 5:
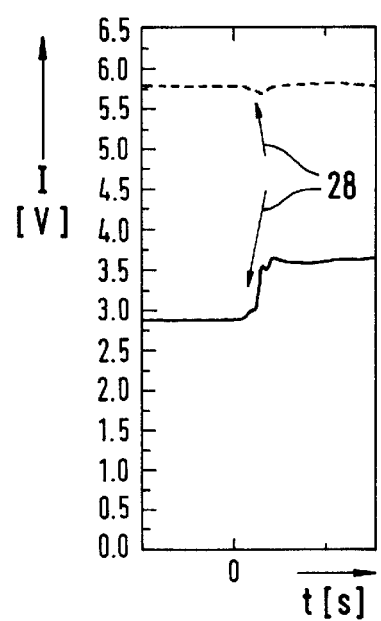
FIG. 5 shows measuring curves during checking of the liquid take up of an analysis element with water as the sample liquid.

The experimental results shown in FIG. 5 correspond to FIG. 4 with the exception that the test layer 5 is not contacted by blood, but by distilled water. While the remission signal given as a dotted line only shows a small drop that is hardly noticeable at the time of contact with the liquid sample, a clear and easily-measurable signal change can be determined for the transversal signal in this case as well. This shows that the invention is in particular suitable in cases where the liquid sample is only slightly or not at all colored.

In the arrangement shown in FIGS. 1 to 3, layer 4 is positioned on the side of the foil segment 6 facing away from the light source 11. The test layer is therefore illuminated through the foil segment. With such a design it is no problem to stack one or more additional layers on top of the test layer 5 in contact with the foil segment 6. For example, the test field 4 may have three layers—the first serving to separate the red blood corpuscles, the second containing a reagent causing a preliminary reaction, and the third layer in contact with the foil segment 6 being a color reaction layer containing the reagents for a color reaction. This example shows that the liquid, whose take up is to be checked in the layer next to the foil segment, is not necessarily the original liquid sample. Rather, it may be a sample liquid, which is modified during preparatory stages (especially plasma obtained by separating the red blood corpuscles from the blood).

Figure 6:
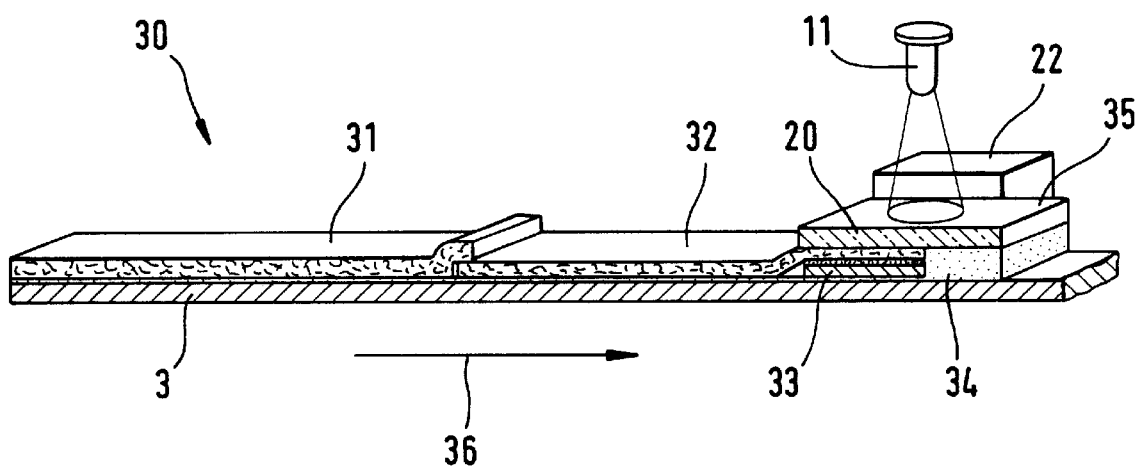
FIG. 6 shows a perspective principle presentation of a preferred embodiment for checking liquid take up in a test carrier with longitudinal transport.

FIG. 6 illustrates further advantageous variation possibilities. It shows an analysis element 30 with longitudinal liquid transport, in which several test layers 31 to 33 are at least partially arranged next to each other on a base strip 3. They are arranged in such a way that a liquid sample applied onto the first test layer 31 is transported lengthways across the test layers (from left to right in the figure)—similar to a chromatography process. The liquid sample is transported to an evaluation zone where a reaction required for the analysis takes places. Further details about such types of analysis elements are described, for example, in U.S. Pat. No. 5,110,550. Checking liquid take up refers, in this case, too, to the last test layer in the direction of flow. The path of the liquid flow ends at the right end of the test layer 32 as seen from the figure. Reference number 34 designates a melt adhesive strip, by means of which a transparent foil segment 35 is affixed, which is relatively rigid, so that the right part of the test layer 32 and the test layer 33 underneath are held downwards by the foil segment 35.

The foil segment 35 is therefore also designated as a holding-down layer. This example shows that the invention is also suitable in those cases where the contact required between the test layer 33 and the foil segment 35 is not made by coating or any other direct connection, but in a different way, for example, by an adhesive strip provided on the edge.

With an analysis element, in which the liquid is transported in a defined direction (symbolized by the arrow 36 in FIG. 6) parallel to the main surface direction of a test layer, it is advantageous if—as shown—the light source is directed onto an area of the test layer at its downstream end in the direction of take up 36. The light emerging here from the circumferential surface 22 is detected analogues with the construction shown in FIG. 3 using a light checking receiver 22.

Although the invention has been described in detail with reference to a preferred embodiment, variations and modifications exist within the scope and spirit of the invention as described and defined in the following claims.

We claim:

1. A method for checking the taking up of a liquid by an absorbent test layer of an analysis element, which absorbent test layer is in contact with a segment of optically transparent foil, the method comprising the steps of:
    taking up liquid by absorption in the test layer,
    illuminating the test layer with primary light, and
    detecting secondary light emerging from the circumferential surface of the foil segment of the analysis element for generating a light signal which is characteristic of the liquid take up by absorption in the test layer.

2. Method according to claim 1, wherein the test layer is illuminated through the foil segment.

3. Method according to claim 1, wherein the test layer includes upstream and downstream ends and the liquid is taken up into the test layer in a defined direction parallel to the main surface direction of the test layer, and an area of the test layer at its downstream end in the direction of take up is illuminated with primary light.

4. Method according to claim 1, wherein the test layer is fly connected to the foil segment, whereby the foil segment forms a test layer carrier foil for the test layer.

5. Method of claim 4, wherein the foil segment is coated with the test layer.

6. Method of claim 5, wherein the test layer contains a dispersion film former and a pigment.

7. An analytical system comprising
    at least one analysis element having an absorbent test layer in surface contact with an optically transparent foil segment having a circumferential surface,
    an evaluation instrument with a light source directed onto the test layer, by which the test layer located in a measuring position in the evaluation instrument is illuminated with primary light, the evaluation instrument further including evaluation electronics adapted for generating information about the take up of liquid by the absorbent test layer on the basis of a change of the light signal during take up of the liquid, and
    a light receiver adapted and arranged for detecting secondary light emerging from the analysis element and to generate a light signal and is further adapted and arranged such that the light receiver and the circumferential surface are juxtaposed and the light receiver detects secondary light emerging from the circumferential surface of the foil segment.

8. Analytical system according to claim 7, wherein the test layer is in the measuring position of the analysis element positioned on the side of the foil segment facing away from the light source so that the test layer is illuminated through the foil segment.

9. Analytical system according to claim 7, wherein the test layer is adapted and arranged to take up liquid in a defined direction parallel to the main surface direction of the test layer, and the light source is directed on an area of the test layer at its downstream end in the direction of taking up.

10. Analytical system according to claim 7, wherein the test layer is fly connected to the foil segment, whereby the foil segment forms a test layer carrier foil for the test layer.

11. Analytical system according to claim 10, wherein the foil segment is coated with the test layer.

12. Analytical system according to claim 11, wherein the test layer contains a dispersion film former and a pigment.

13. Method according to claim 1, wherein the secondary light emerging from the circumferential surface of the foil segment generates a transversal signal and further comprising the steps of detecting secondary light diffusely reflected by the test layer thereby generating a remission signal and setting the remission signal and the transversal signal in relation to each other to check complete liquid take up.

14. Method according to claim 1, wherein the light receiver and the circumferential surface are juxtaposed.

15. A method for analyzing a sample liquid, the method comprising the steps of:
    providing an analysis element having at least one test layer of absorbent material, which test layer is fixed to the analysis element and is in contact with a segment of an optically transparent foil,
    contacting the analysis element with the sample liquid,
    absorbing a quantity of the sample liquid into the test layer, said quantity corresponding to the absorbency of the test layer, and
    checking the taking up of the sample by the absorbent test layer, said checking step comprising
    a) illuminating the test layer with primary light,
    b) detecting secondary light emerging from the circumferential surface of the foil segment thereby generating a transversal signal and
    c) generating a signal characteristic of the liquid take up from the transversal signal.

16. Method according to claim 15 in which secondary light diffusely reflected by the test layer is detected thereby generating a remission signal and the step of generating a signal characteristic of the liquid take up comprises a step of setting the remission signal and the transversal signal in relation to each other.

17. Method of claim 15 wherein secondary light is detected from opposite sectional areas of the circumferential surface of the foil segment.

18. Method of claim 15 wherein the test layer is illuminated through the foil segment.

19. Method of claim 15 wherein the test layer includes upstream and downstream ends and the liquid is taken up into the test layer in a defined direction parallel to the main surface direction of the test layer, and an area of the test layer at its downstream end in the direction of take up is illuminated with primary light.

20. Method of claim 15 wherein the test layer is firmly connected to the foil segment, whereby the foil segment forms a test layer carrier foil for the test layer.

21. Method of claim 20, wherein the foil segment is coated with the test layer.

22. Method of claim 21, wherein the test layer contains a dispersion film former and a pigment.

23. An analytical system comprising
    an analysis element having at least one test layer of absorbent material, which test layer is fixed to the analysis element and is in contact with a segment of an optically transparent foil, and
    an evaluation instrument formed to check the taking up of the sample by the absorbent test layer, the evaluation instrument including evaluation electronics comprising
    a) means for illuminating the test layer with primary light,
    b) means for detecting secondary light emerging from the circumferential surface of the foil segment thereby generating a transversal signal and c) means for generating a signal characteristic of the liquid take up from the transversal signal.

24. The system of claim 23 wherein the evaluation instrument further comprises means for generating a remission signal from the secondary light diffusely reflected by the test layer and means for generating a signal characteristic of the liquid take up by setting the remission signal and the transversal signal in relation to each other.

25. The system of claim 23, wherein the detecting means detects secondary light emerging from opposite sectional areas of the circumferential surface of the foil segment.

26. The system of claim 23 wherein the test layer is in the measuring position of the analysis element positioned on the side of the foil segment facing away from the light source so that the test layer is illuminated through the foil segment.

27. The system of claim 23 wherein the test layer is adapted and arranged to take up liquid in a defined direction parallel to the main surface direction of the test layer, and the light source is directed on an area of the test layer at its downstream end in the direction of taking up.

28. The system of claim 23 wherein the test layer is firmly connected to the foil segment, whereby the foil segment forms a test layer carrier foil for the test layer.

29. The system of claim 28 wherein the foil segment is coated with the test layer.

30. The system of claim 29 wherein the test layer contains a dispersion film former and a pigment.

31. The method of claim 1, wherein secondary light is detected from opposite sectional areas of the circumferential surface of the foil segment.

32. The method of claim 7, wherein the light receiver detects secondary light emerging from opposite sectional areas of the circumferential surface of the foil segment.

* * * * *